(12) United States Patent
Doi et al.

(10) Patent No.: US 7,651,595 B2
(45) Date of Patent: Jan. 26, 2010

(54) ANALYZING TOOL WITH KNOB PART

(75) Inventors: Shigeru Doi, Kyoto (JP); Yoshimitsu Morita, Kyoto (JP)

(73) Assignee: Arkray, Inc., Kyoto (JP)

( * ) Notice: Subject to any disclaimer, the term of this patent is extended or adjusted under 35 U.S.C. 154(b) by 614 days.

(21) Appl. No.: 10/545,394

(22) PCT Filed: Feb. 13, 2004

(86) PCT No.: PCT/JP2004/001594

§ 371 (c)(1),
(2), (4) Date: Apr. 26, 2006

(87) PCT Pub. No.: WO2004/072632

PCT Pub. Date: Aug. 26, 2004

(65) Prior Publication Data

US 2006/0243589 A1 Nov. 2, 2006

(30) Foreign Application Priority Data

Feb. 14, 2003 (JP) .............................. 2003-037031

(51) Int. Cl.
G01N 27/403 (2006.01)
G01N 27/327 (2006.01)
G01N 27/333 (2006.01)
(52) U.S. Cl. .................. 204/400; 204/403.01; 204/416
(58) Field of Classification Search .............. 204/403.01–403.15; 205/777.5, 778, 792; 422/55–57
See application file for complete search history.

(56) References Cited

U.S. PATENT DOCUMENTS

| 5,126,034 | A | * | 6/1992 | Carter et al. | ........... 204/403.05 |
| 5,320,732 | A | | 6/1994 | Nankai et al. | ........... 204/403.04 |
| 5,354,447 | A | | 10/1994 | Uenoyama et al. | ........ 205/777.5 |
| 5,425,360 | A | * | 6/1995 | Nelson | ........................ 600/323 |
| 6,066,243 | A | * | 5/2000 | Anderson et al. | ........ 422/82.01 |
| 6,168,699 | B1 | * | 1/2001 | Frenkel et al. | ......... 204/403.14 |
| 6,258,229 | B1 | * | 7/2001 | Winarta et al. | ......... 204/403.04 |
| 6,830,669 | B2 | | 12/2004 | Miyazaki et al. | ............ 204/409 |
| 6,985,764 | B2 | * | 1/2006 | Mason et al. | ................ 600/344 |

FOREIGN PATENT DOCUMENTS

| JP | 2-310457 | 12/1990 |
| JP | 4-357449 | 12/1992 |
| JP | 5-164724 | 6/1993 |
| JP | 11-64226 | 3/1999 |
| JP | 2001-159618 | 6/2001 |
| WO | WO 00/73778 | 12/2000 |

OTHER PUBLICATIONS

JPO computer English language translation of Tadahisa JP 11-064226 A downloaded Apr. 26, 2009.*

* cited by examiner

Primary Examiner—Alex Noguerola
(74) Attorney, Agent, or Firm—Hamre, Schumann, Mueller & Larson, P.C.

(57) ABSTRACT

The present invention relates to a test tool (X1) attached to an analyzing device (1) for analyzing a sample. The test tool (X1) includes a pinching portion (6) for attachment to the analyzing device (1) or removal from the analyzing device (1). The pinching portion (6) may include recesses or projections.

12 Claims, 8 Drawing Sheets

ANALYZING TOOL WITH KNOB PART

This application is a 371 of application no. PCT/JP2004/001594, filed on Feb. 13, 2004, which claims foreign priority from Japanese application no. 2003-37031, filed on Feb. 14, 2003.

TECHNICAL FIELD

The present invention relates to an analyzing tool attached to an analyzing device for sample analysis.

BACKGROUND ART

Simplified measuring devices that can be held in a hand have been widely used for facilitating the measurement of blood-sugar level at or away from home. An example of such simplified blood-sugar level measuring device is shown in FIG. 8. A biosensor 9 is attached to the measuring device and blood is supplied to the biosensor 9, whereby the blood-sugar level is measured by an electrochemical method.

As shown in FIG. 9, the biosensor 9 has a plate-like form as a whole, and includes an insulating base plate 90 on which a cover 92 is laminated via a spacer 91 (see JP-A-2001-159618, for example). The biosensor 9 further includes an end formed with a blood inlet 93, and the blood inlet 93 is communicated with an outlet 95 via a capillary 94. With such an arrangement, blood introduced from the blood inlet 93 moves in the capillary 94 toward the outlet 95. Such biosensor 9 is pinched by a user at a side surface 96 or upper and lower surfaces 97A, 97B of the biosensor 9, to be attached or removed relative to a blood-sugar measuring device 8 (see FIG. 8).

However, as the biosensor 9 is relatively small and the side surface 96 and the upper and lower surfaces 97A, 97B of the biosensor 9 are typically flat, attaching and removing of the biosensor 9 is not always easy. For example, if a portion where the user pinches and its vicinity at the biosensor 9 is a flat surface, the biosensor 9 may slip out of fingertips, and a relatively large strength is necessary for removing the biosensor 9 from the blood-sugar measuring device 8 (see FIG. 8). Thus, the removal of the biosensor 9 may be a large load especially for aged people with weakened muscle strength.

Further, as the conventional biosensor 9 does not define the portion for pinching the biosensor 9, the user optionally pinches the side surface 96 or the upper and lower surfaces 97A, 97B of the biosensor 9. Thus, when removing the biosensor 9 from the blood-sugar measuring device 8 (see FIG. 8), the finger may contact the blood inlet 93 or the outlet 95, and thus the blood may adhere to the fingertip. In a hospital, for example, when measuring blood of a plurality of patients, it is a hygienic problem that blood of a patient adheres to the user's fingertip. The user needs to handle the biosensor 9 without adherence of the patient's blood when removing the biosensor 9, which is another problem in handling of the biosensor 9.

DISCLOSURE OF THE INVENTION

An object of the present invention is to improve handling of a test tool (a biosensor for example) on attachment or removal with respect to an analyzing device such as a blood-sugar measuring device.

A test tool provided by the present invention is attached to an analyzing device for sample analysis, and attached to or removed from the analyzing device by hand. The test tool comprises a pinching portion used for attachment to the analyzing device or for removal from the analyzing device.

The pinching portion may include a recess or a projection.

Preferably, the test tool may further comprise an end inserted into the analyzing device for the attachment to the analyzing device. The recess or the projection is concave or convex across the inserting direction of the test tool.

Preferably, the test tool has an entirely plate-like form. The recess or the projection is inwardly concave or outwardly convex in thicknesswise of the test tool.

Preferably, the recess or the projection includes a curved surface for contact with a fingertip.

Preferably, the test tool is attached to an analyzing device having a plurality of terminals and an analyzing circuit. The test tool comprises a plurality of electrodes brought into contact with the terminals when attached to the analyzing device. At least one of the electrodes serves as a counter-disturbance noise electrode that is more likely to receive disturbance noise than other electrodes. The counter-disturbance noise electrode may partly be exposed at the pinching portion.

Preferably, the electrodes include a first electrode electrically connected to the analyzing circuit, and also include a second electrode cooperating with the first electrode to apply a voltage across a target portion at the test tool. The second electrode works as the counter-disturbance noise electrode.

The electrodes may include first and second electrodes electrically connected to the analyzing circuit for applying a voltage across target portions of the test tool, and a third electrode for working against disturbance noise but not for the apply of a voltage across the target portion of the test tool. Preferably, the third electrode is not electrically connected to the analyzing circuit when the test tool is attached to the analyzing device.

Preferably, one of the terminals of the analyzing device is grounded as a ground connection terminal. The counter-disturbance noise electrode contacts with the ground connection terminal when the test tool is attached to the analyzing device.

Preferably, the counter-disturbance noise electrode is arranged to surround at least one of the electrodes other than the counter-disturbance noise electrode.

Preferably, the test tool further comprises a path for moving the sample; a base plate formed with the electrodes; and a cover connected to the base plate and formed with an outlet for discharging air out of the path. The counter-disturbance noise electrode is formed along an edge of the base plate.

Preferably, the counter-disturbance noise electrode contacts a corresponding one of the terminals prior to the other electrodes than the counter-disturbance noise electrode, when the test tool is attached to the analyzing device.

Preferably, the test tool is designed as a biosensor for analyzing a specific component in blood or urine, for example. Examples of the specific component are glucose, cholesterol, and lactic acid.

BEST MODE FOR CARRYING OUT THE INVENTION

First, a biosensor according to a first embodiment of the present invention is described with reference to FIGS. 1-6.

Figure 1:
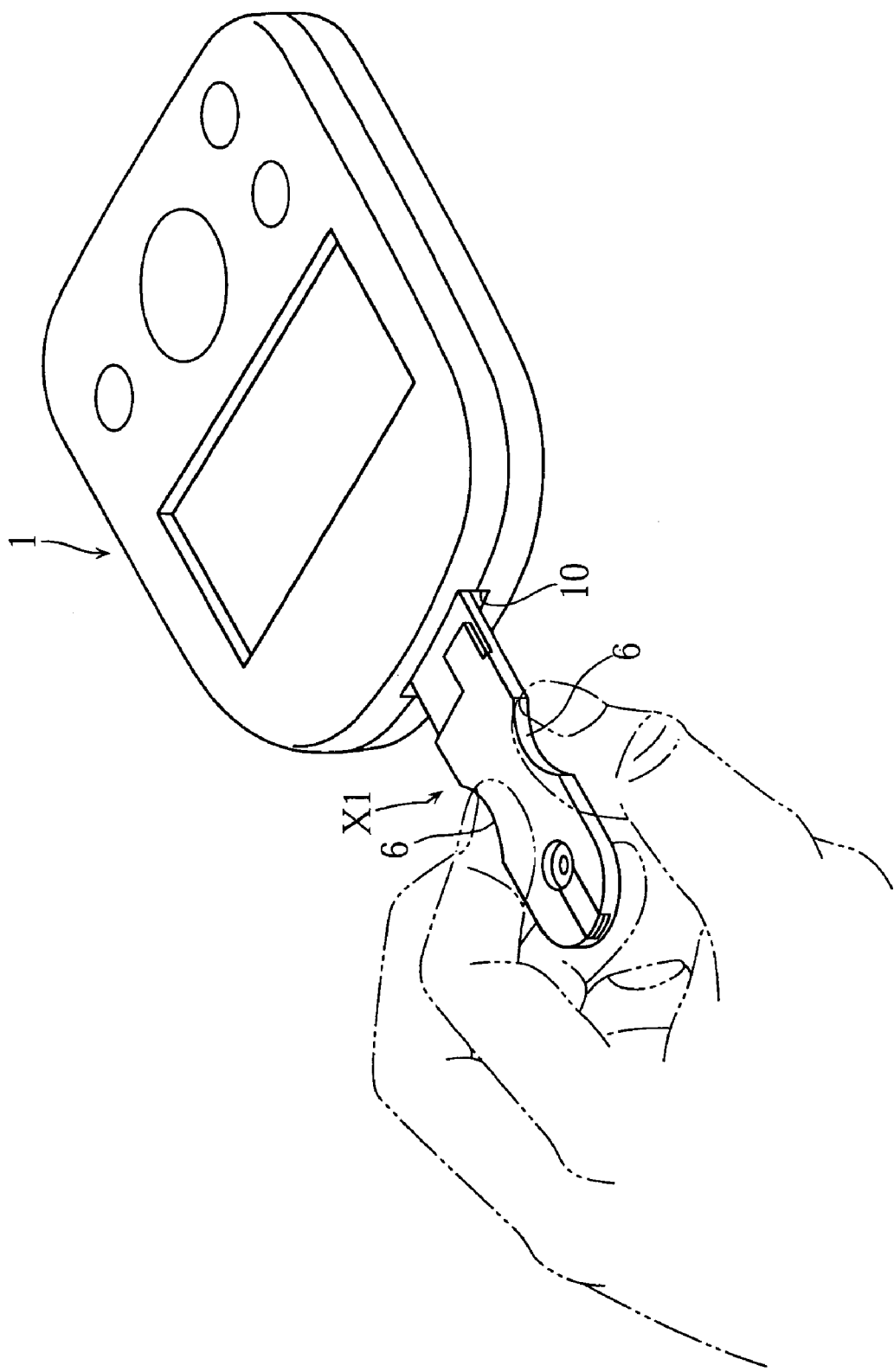
FIG. 1 is an overall perspective view illustrating a biosensor according to a first embodiment of the present invention, when attached to an analyzing device.
Figure 2:
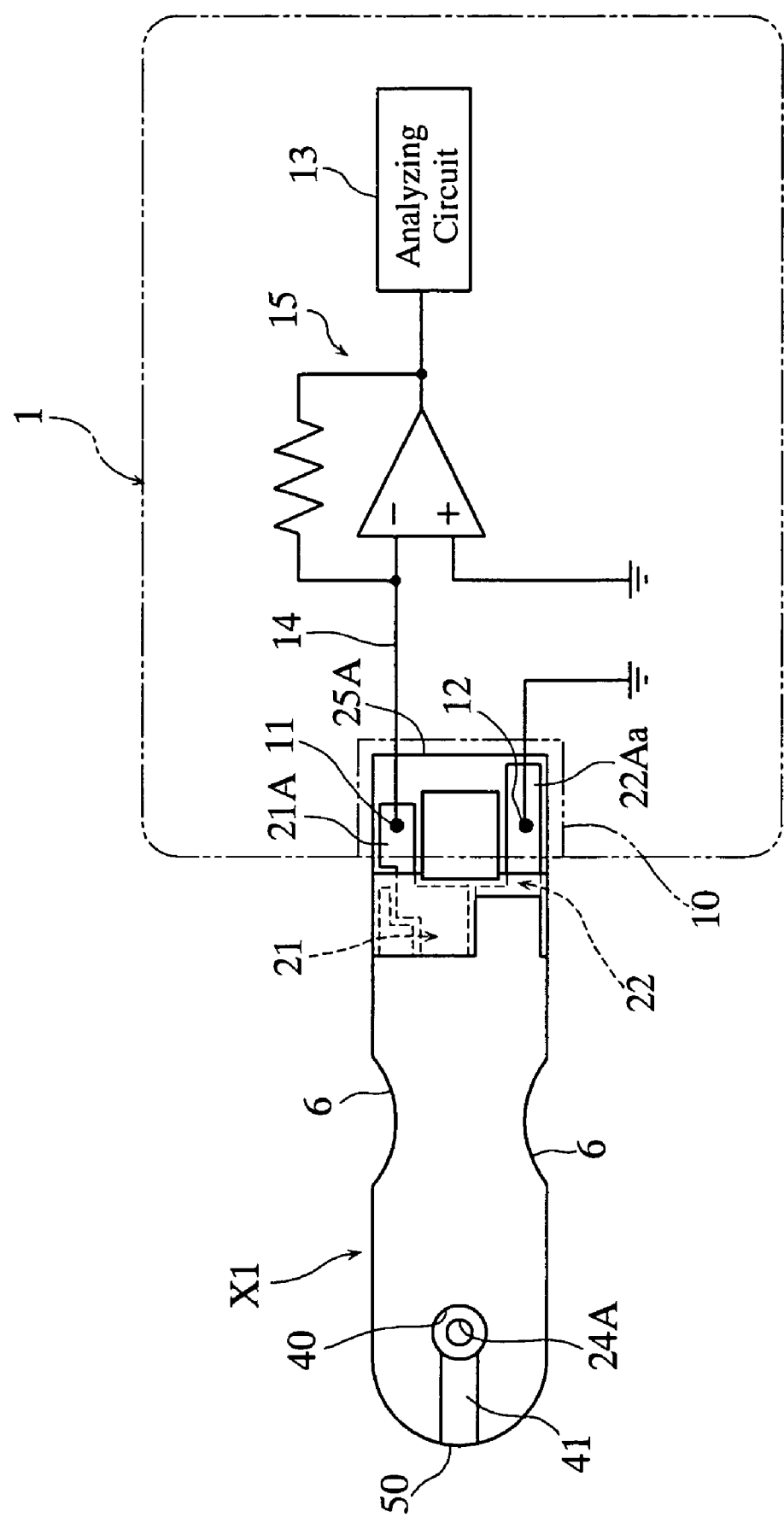
FIG. 2 is partly a plan view illustrating the biosensor of FIG. 1, and partly a block diagram illustrating the analyzing device.
Figure 3:
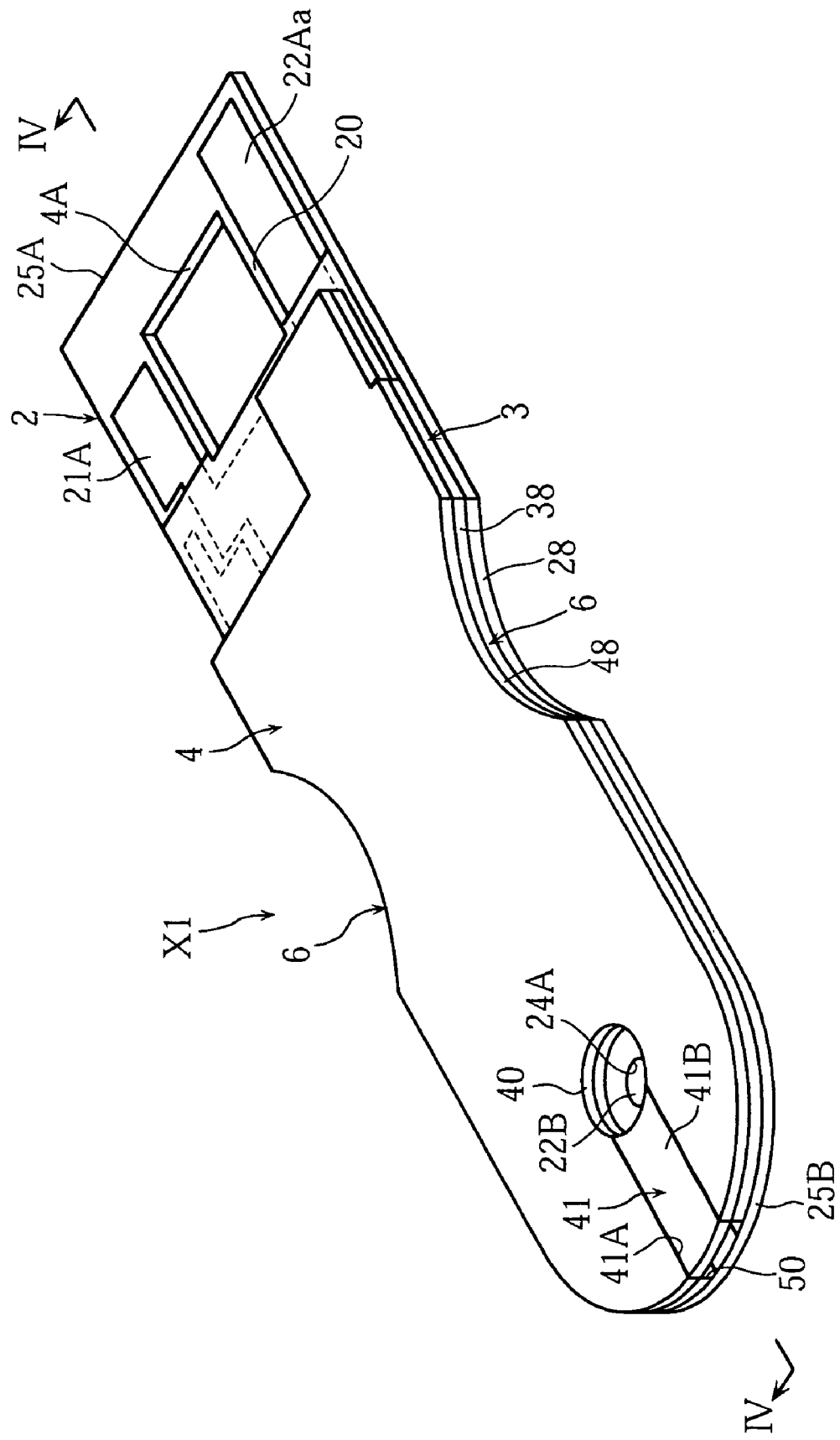
FIG. 3 is an overall perspective view illustrating the biosensor shown in FIGS. 1 and 2.
Figure 4:
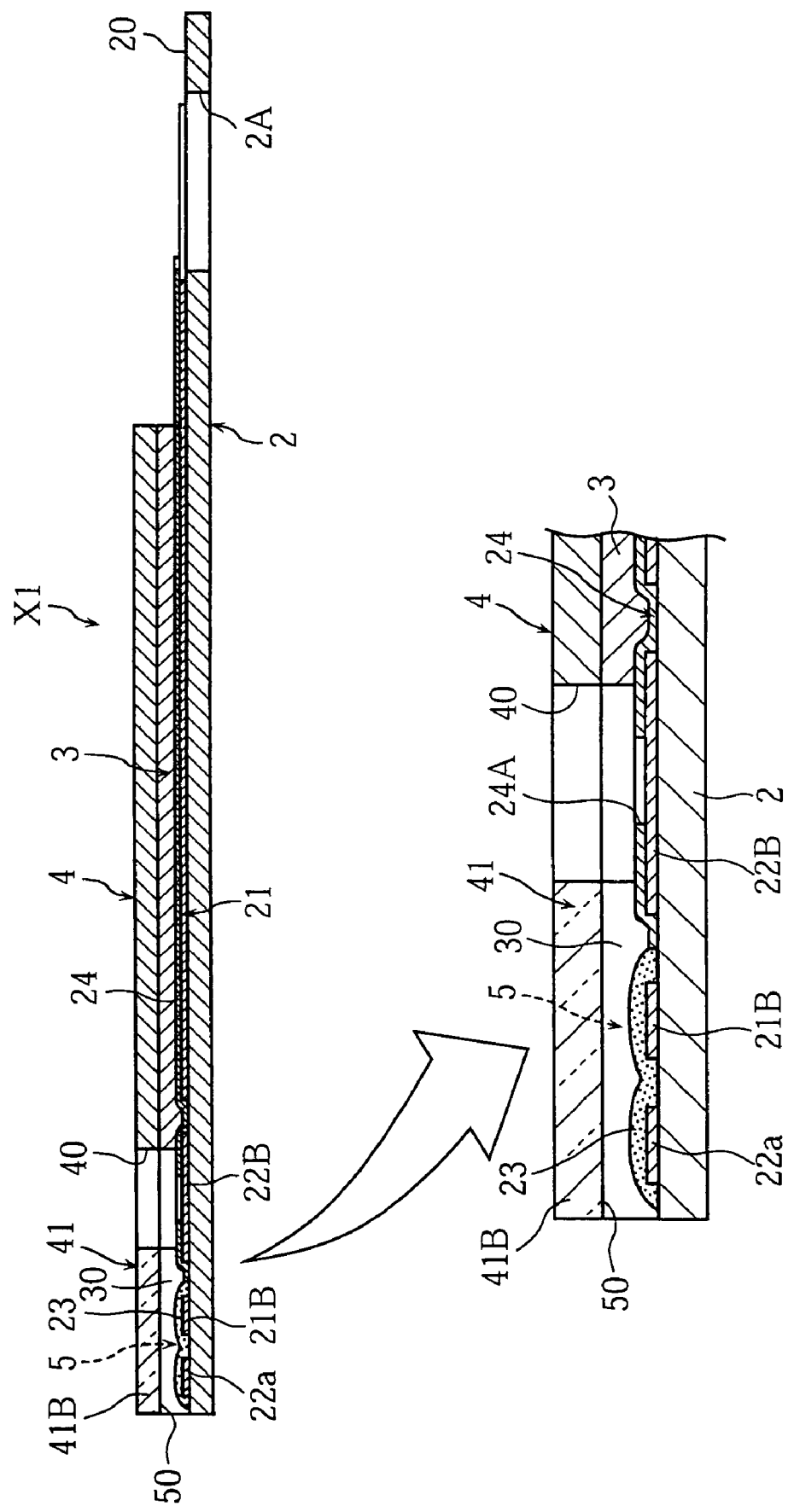
FIG. 4 is a sectional view taken along line IV-IV in FIG. 3, and an enlarged view illustrating a principal part.

As shown in FIGS. 1 and 2, a disposable biosensor X1 is attached to a connector 10 of an analyzing device 1 in use. As shown in FIGS. 3 and 4, the biosensor X1 includes a base plate 2 having an upper surface 20 on which a cover 4 is laminated via a spacer 3. These components 2-4 integrally form a path 5 and a pinching portion 6.

Figure 5:
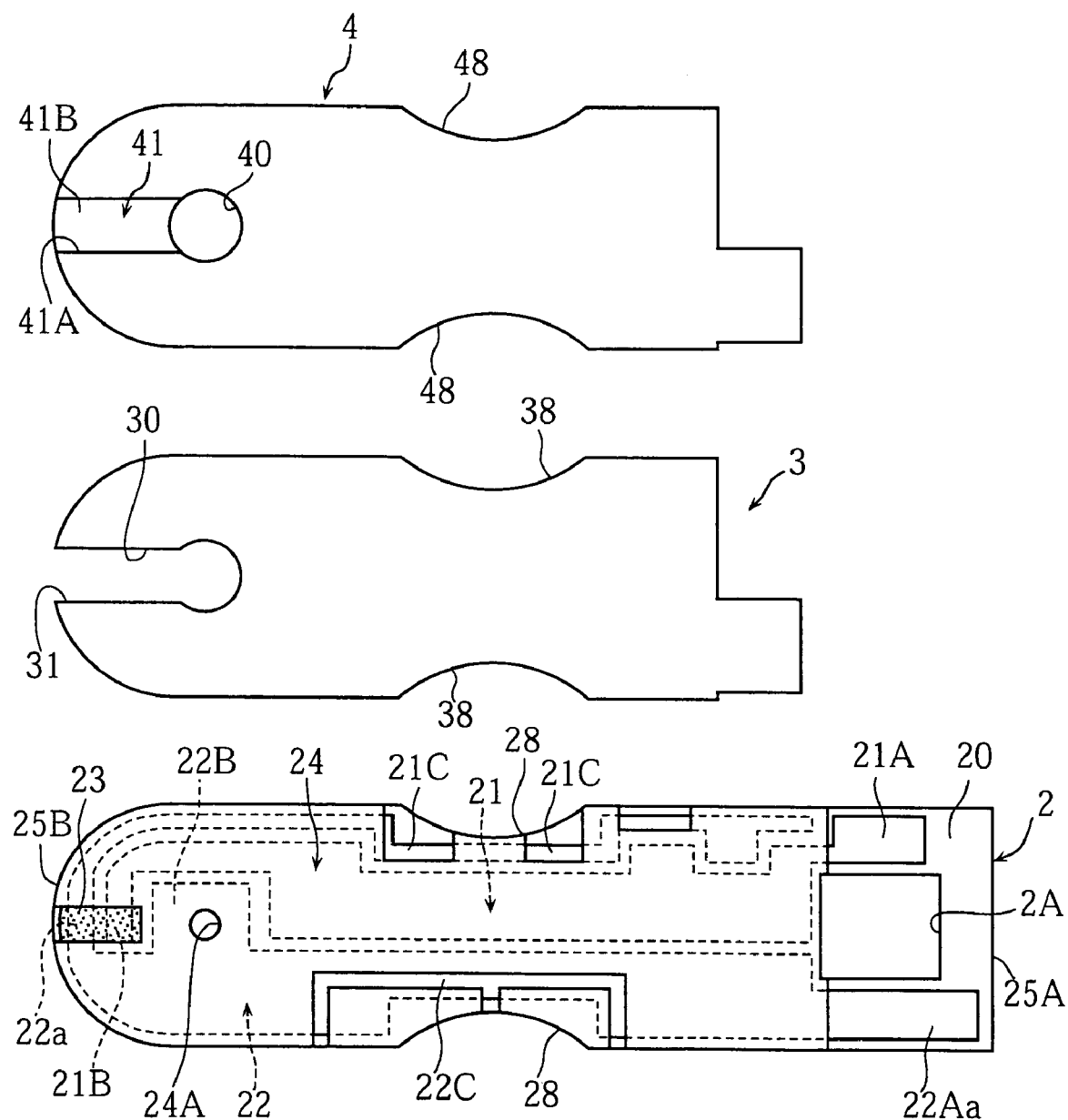
FIG. 5 is an exploded plan view illustrating the biosensor of FIG. 3.

As shown in FIG. 5, the spacer 3 is formed with a slit 30 which includes an opening at its tip end, to define the size of the path 5. Specifically, the width and the length of the path 5 are defined by the slit 30. The opening 31 at the tip end of the slit 30 forms a sample inlet 50 for introducing a sample in the path 5.

As shown in FIGS. 3-5, the cover 4 includes an outlet 40 and a window 41. As seen from FIG. 4, the outlet 40 communicates with the inner part of the path 5 to discharge inner air of the path 5 outside. The window 41 is formed between the sample inlet 50 and the outlet 40, as viewed in plan of the biosensor X1, for checking the entrance of the sample into the path 5 as will as the movement of the sample in the path 5. Such window 41 is made by forming a cutout 41A at the cover 4 and then providing a transparent member 41B at the cutout 41A.

Figure 6:
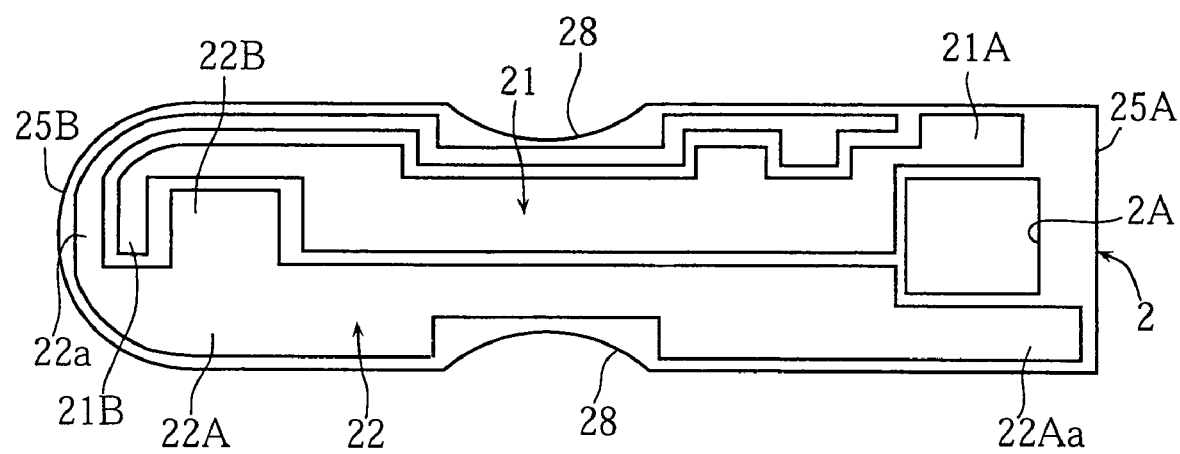
FIG. 6 is a plan view illustrating a working electrode and a counterpart electrode of the biosensor.

As shown in FIGS. 5 and 6, the base plate 2 is made by an insulating material and is elongated in a (longitudinal) direction. The base plate 2 includes a through-hole 2A formed at a portion where the cover 4 is not laminated. The through-hole 2A is used by the analyzing device 1 (see FIGS. 1 and 2) to obtain information about the biosensor X1 such as an item number, for example. Specifically, the analyzing device 1 obtains such item number by recognizing the presence or absence, the size, or the position of the through-hole 2A. The upper surface 20 of the base plate 2 is formed with a working electrode 21, a counter electrode 22, a reagent portion 23, and an insulating film 24.

The working electrode 21 is used together with the counter electrode 22 for applying a voltage across a reaction field. The working electrode 21 is entirely elongated in lengthwise of the base plate 2. The working electrode 21 includes an end 21A arranged in the vicinity of an end 25A of the base plate 2. The end 21A contacts a first terminal 11 (see FIG. 2) of the analyzing device 1 when the biosensor X1 is attached to the analyzing device 1, as described later. The working electrode 21 further includes an end 21B protruding in widthwise of the base plate 2, in the vicinity of a circular end 25B of the base plate 2.

The counter electrode 22 is for working against disturbance noise, and includes a hairpin main portion 22A formed along the circumference of the base plate 2 and also includes a peninsular portion 22B protruding from the main portion 22A. The end 21B of the working electrode 21 is sandwiched between a corner 22a of the main portion 22A and the peninsular portion 22B, while the counter electrode 22 surrounds the entire working electrode 21. The main portion 22A includes an end 22Aa arranged in the vicinity of the end 25A of the base plate 2. The end 22Aa contacts a second terminal 12 of the analyzing device 1 when the biosensor X1 is attached to the analyzing device 1, as described later, while being arranged at a portion nearer to the end 25A of the base plate 2 than the portion where the end 21A of the working electrode 21 (see FIG. 2) is arranged. The peninsular portion 22B is positioned right below the outlet 40 as viewed in plan of the biosensor X1, and has a plain surface larger than the outlet 40.

The reagent portion 23 bridges between the end 21B of the working electrode 21 and the corner 22a of the main portion 22A. The reagent portion 23 is a solid including an oxidoreductase and an electron mediator for example, and dissolves when the sample is supplied. The oxidoreductase and the electron mediator are selected according to a target component. For example, when measuring the glucose concentration, glucose dehydrogenase or glucose oxidase is used as the oxidoreductase, and potassium ferricyanide is used as the electron mediator.

As shown in FIG. 5, the insulating film 24 covers the most part of the working electrode 21 and the counter electrode 22. Exposed portions, which are not covered by the insulating film 24, on the working electrode 21 and the counter electrode 22 are the ends 21A, 22A, the end 21B and the corner 22a formed with the reagent portion 23, and portions 21C, 22C in the vicinity of the pinching portion 6. The insulating film 24 is formed with a through-hole 24A at a portion facing the peninsular portion 22B of the counter electrode 22, whereby a part of the peninsular portion 22B is also exposed, without the insulating film 24.

The path 5 moves the sample by the capillary action, and also provides a reaction field. As shown in FIGS. 4 and 5, the path 5 is elongated longitudinally of the base plate, while crossing the end 21B of the working electrode 21 and the corner 22a of the main portion 22A. In this state, the reagent portion 23 is arranged in the path 5.

As shown in FIG. 1, the pinching portion 6 is used by a user to hold the biosensor X1 when attaching the biosensor X1 to the analyzing device 1, or when removing the biosensor 1 from the analyzing device 1. As shown in FIGS. 3 and 5, pinching portion 6 includes recesses each having a circular curved surface which includes cutouts 28, 38, 48 formed in the same shape respectively at the base plate 2, the spacer 3, and the cover 4.

The analyzing device 1 with the biosensor X1 performs analysis of the sample in an electrochemical method. As shown in FIGS. 1 and 2, the analyzing device includes a connector 10 for attaching the biosensor X1, and an analyzing circuit 13 which performs calculation, based on the information obtained from the connector 10, for analyzing a specific component in the sample. As shown in FIG. 2, the connector 10 includes first and second terminals 11, 12. The first terminal 11 contacts with the end 21A of the working electrode 21, while the second terminal 12 contacts with the end 22Aa of the counter electrode 22. The first terminal 11 is electrically connected to the analyzing circuit 13 via a signal line 14, and a current-voltage converter 15 is provided on the signal line 14. The current-voltage converter 15 converts a current value obtained from the biosensor X1 to a voltage value which is to be entered into the analyzing circuit 13. On the other hand, the second terminal 12 is connected to the ground.

In sample analysis using the biosensor X1, the biosensor X1 is attached to the analyzing device 1 as shown in FIG. 1, and then a sample (typically blood or urine) is introduced into the sample inlet 50 of the biosensor X1. In attaching the biosensor X1, the biosensor X1 is held at the pinching portion 6 by fingertips, and then the end 25A (see FIG. 3) of the biosensor X1 is inserted into the connector 10 of the analyzing device 1.

As shown in FIG. 2, when the biosensor X1 is attached to the analyzing device 1, each of the ends 21A, 22Aa of the working electrode 21 and the counter electrode 22 of the biosensor X1 comes into contact with a respective one of the first and second terminals 11, 12 of the analyzing device 1. The end 22Aa of the counter electrode 22 of the biosensor 1 is arranged at the portion nearer to the end 25A of the base plate 2 than the portion where the end 21A of the working electrode 21 is arranged. With such an arrangement, as may be assumed from FIG. 2, in the process of attaching the biosensor X1 to the analyzing device 1, the end 22Aa of the counter electrode 22 first contacts the second terminal 12, and then the end 21A of the working electrode 21 contacts the first terminal 11.

Next, as assumed from FIG. 4, the sample supplied to the biosensor X1 moves in the path 5 toward the outlet 40 due to the capillary action, whereby the inside of the path 5 is filled with the sample. Here, the reagent portion 23 is dissolved by the sample and a solution phase reaction system is established in the path 5. Thereafter, for example, a direct-current power supply (not shown) of the analyzing device 1 applies a voltage across the solution phase reaction system via the first and second terminals 11, 12, and via the working electrode 21 and the counter electrode 22 of the analyzing device 1, as seen from FIG. 2. Then, a current response obtained here is converted into a voltage value by the current-voltage converter 15, and next converted into a digital signal by a non-illustrated AD converter, and finally inputted to the analyzing circuit 13. Based on the digital signal corresponding to the current response, the analyzing circuit 13 performs a calculation for analyzing the sample, for example, for obtaining the glucose concentration in blood.

As the biosensor X1 is disposable, the biosensor X1 needs to be removed from the analyzing device 1 after the calculation at the analyzing circuit 13. The biosensor X1 is removed by holding the biosensor X1 at the pinching portion 6 by fingertips, and then pulling the biosensor X1.

As described above, the pinching portion 6 of the biosensor X1 is used when attaching the biosensor X1 to the analyzing device 1 and when removing the biosensor X1 from the analyzing device 1. In other words, the biosensor X1 is provided with the portion which the user pinches by fingertips for attaching and removing the biosensor X1. This structure facilitates the attaching and removing of the biosensor X1, and prevents the sample from accidentally sticking to fingertips, and thus enables hygienic removal of the biosensor X1. Further, as the pinching portion 6 includes recesses, the biosensor X1 may be prevented from slipping out of fingertips on attaching and removing. This structure also facilitates the handling of the biosensor X1.

Generally, when attaching a biosensor to an analyzing device, static electricity charged at a human body may be conducted to a conductor (a working electrode or a counter electrode) of the biosensor. The biosensor X1 counters such static electricity with the counter electrode 22. Specifically, the counter electrode 22 is formed to surround the working electrode 21 and the outlet 40, and exposed at portions in the vicinity of the outlet 40 and the pinching portion 6, where the static electricity is likely to be conducted to the working electrode 21 and the counter electrode 22. Due to this structure, the static electricity charged at the human body is conducted to the counter electrode 22 prior to the working electrode 21.

As the counter electrode 22 is connected to the ground via the second terminal 12 of the analyzing device 1, the static electricity is sent to the ground via the second terminal 12 to be discharged. Further, as assumed from FIG. 2, on attaching the biosensor X1, the end 22Aa of the counter electrode 22 contacts with the analyzing device 1 before the end 21A of the working electrode 21 contacts therewith. With such an arrangement, the above-described discharge of the static electricity is performed at the moment when the end 22Aa of the counter electrode 22 contacts with the second terminal 12, before the end 21A of the working electrode 21 contacts with the first terminal 11. Thus, when the end 21A of the working electrode 21 contacts the first terminal 11, the static electricity is already discharged from the counter electrode 22. Therefore, the static electricity charged at the counter electrode 22 is prevented from discharging to the working electrode 21, and thus prevented from being inputted to the analyzing circuit 13. As a result, measurement error or measurement deviation due to input of the static electricity into the analyzing circuit 13 can be prevented. Of course, the biosensor X1 can also remove other disturbance noise, not only the static electricity conducted from the human body.

Next, second and third embodiments according to the present invention are described with reference to FIGS. 7A and 7B. In these figures, elements identical to those in the above-described biosensor X1 (see FIGS. 1-6) are given the same reference numbers and duplicated description will be omitted.

Figure 7A:
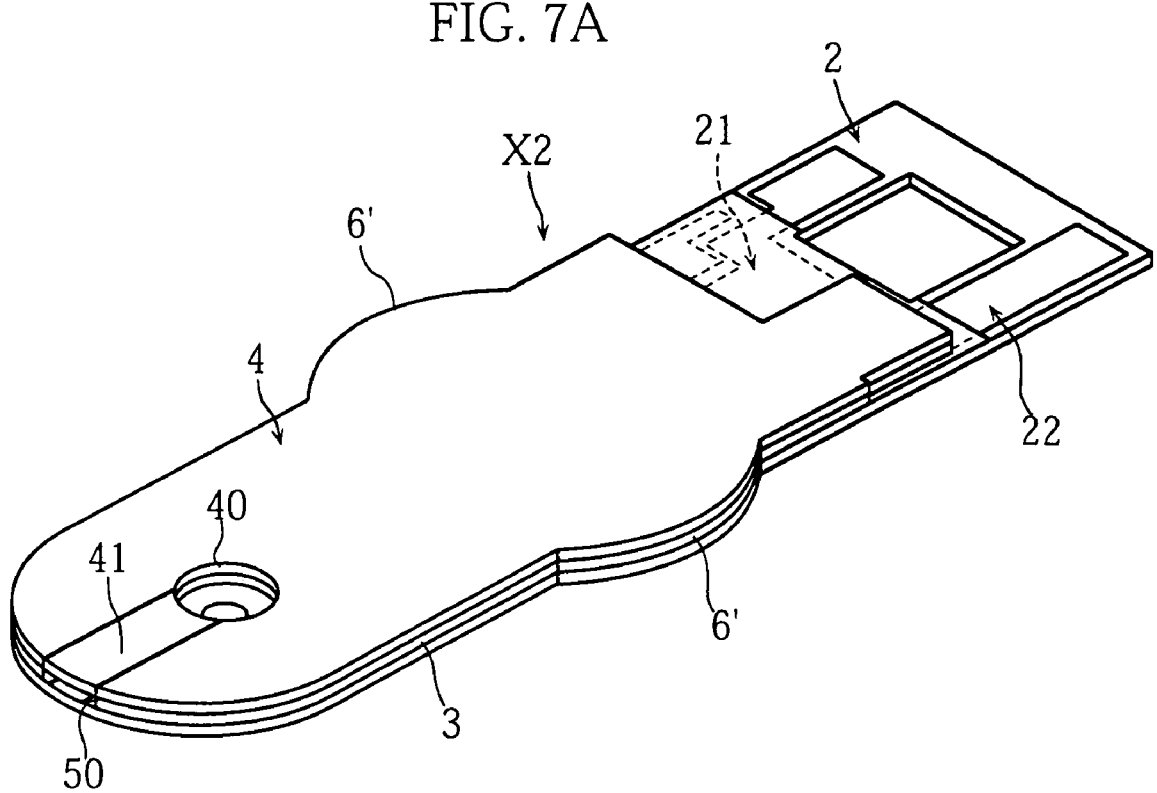
FIG. 7A is an overall perspective view illustrating a biosensor according to a second embodiment.
Figure 7B:
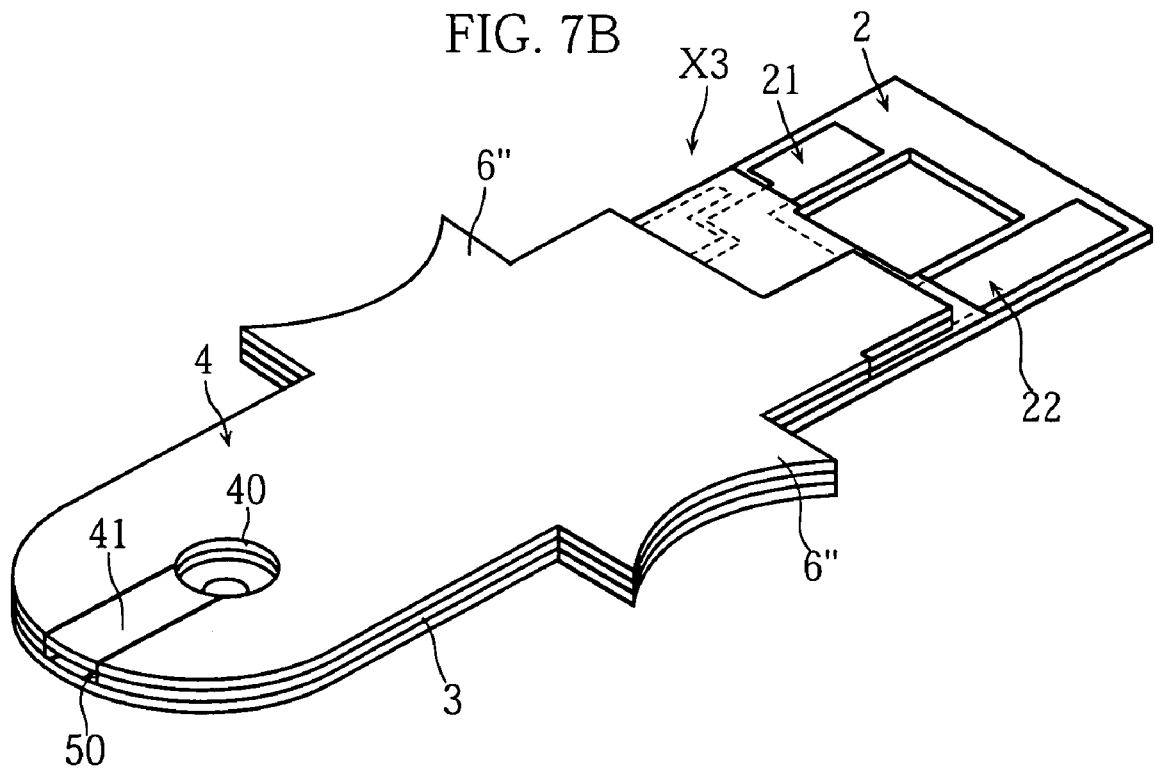
FIG. 7B is an overall perspective view illustrating a biosensor according to a third embodiment.
Figure 8:
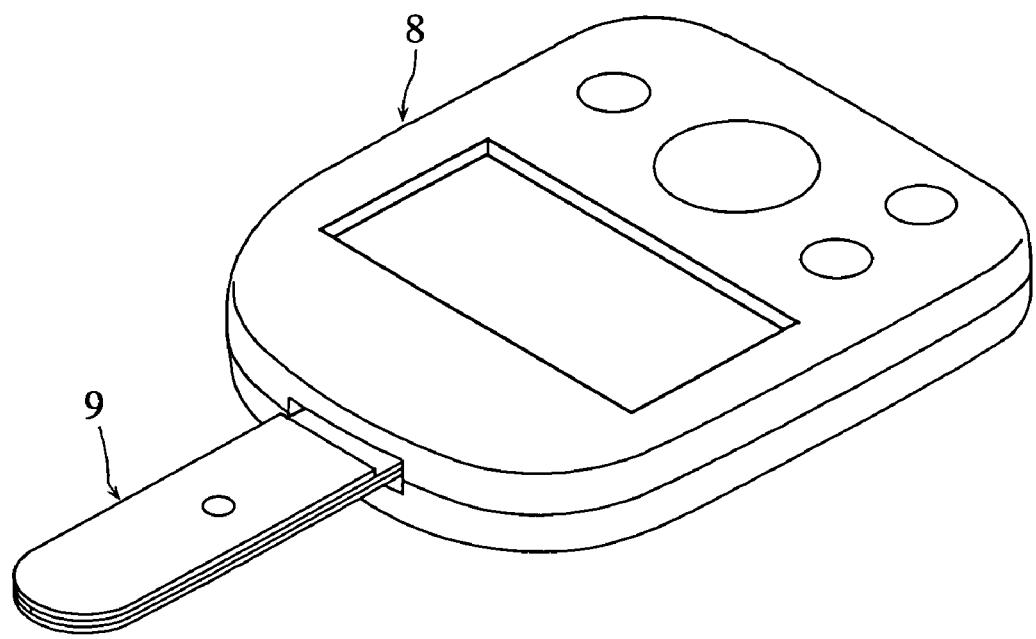
FIG. 8 is an overall perspective view illustrating a conventional biosensor attached to a blood-sugar level measuring device.
Figure 9:
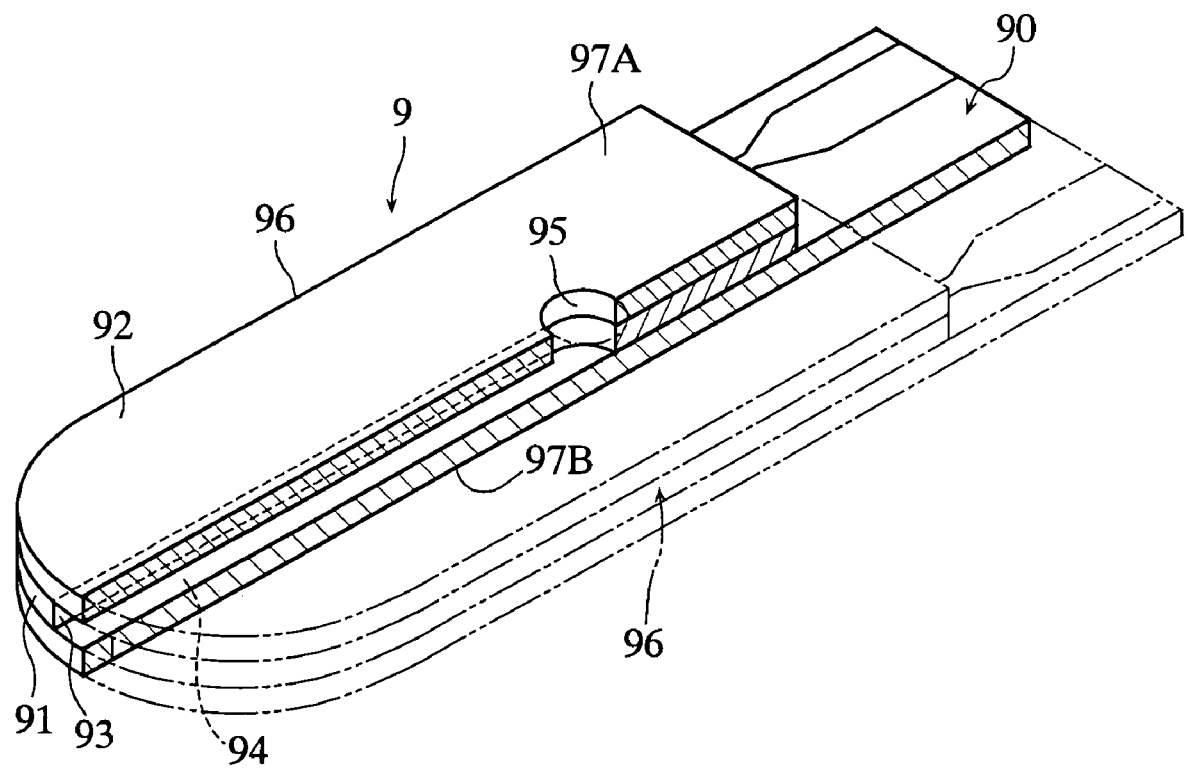
FIG. 9 is a perspective view illustrating an example of conventional biosensor, as partially cutaway.

As shown in FIGS. 7A and 7B, biosensors X2, X3 include pinching portions 6', 6" formed differently from the biosensor X1 (see FIG. 3) according to the first embodiment described above. Specifically, as shown in FIG. 7A, the pinching portion 6' of the biosensor X2 according to the second embodiment projects in widthwise of the biosensor X2 to form projections each including curved surface. On the other hand, as shown in FIG. 7B, the pinching portion 6" of the biosensor X3 according to the third embodiment includes combinations of a projection and a recess, each including curved surfaces.

The biosensors X2, X3 can also be attached and removed relative to the analyzing device using the pinching portions 6', 6" of the biosensors X2, X3, thereby facilitating the handling of the biosensors X2, X3.

The present invention is not limited to the first through third embodiments, but may be modified in various ways. For example, the pinching portion is not limited to the ones described in first through third embodiments, but may include a projection convex in thicknesswise of the biosensor, or a recess concave in thicknesswise of the biosensor. Further, the counter electrode does not necessarily have the function working against disturbance noise, but another electrode may be provided to work against disturbance noise.

The invention claimed is:

1. A test tool attached to an analyzing device far sample analysis, the analyzing device including a plurality of terminals and an analyzing circuit, the test tool being manually attached to or removed from the analyzing device, the test tool comprising:
    a base plate having a pinching recess or projection used for attachment to the analyzing device or for removal from the analyzing device;
    a plurality of electrodes formed on the base plate for contact with the terminals when the test tool is attached to the analyzing device; and
    an insulating film for covering the plurality of electrodes;

wherein at least when one of the electrodes serves as a counter-disturbance noise electrode that is more likely to receive disturbance noises than another electrode, wherein the insulating film does not cover a portion of the counter-disturbance noise electrode located at the pinching recess or projection.

2. The test tool according to claim 1, wherein the base plate includes an end inserted into the analyzing device for the attachment to the analyzing device, wherein the pinching recess or the pinching projection is concave or convex across an inserting direction of the test tool.

3. The test tool according to claim 1, wherein the pinching recess or the pinching projection is inwardly concave or outwardly convex in widthwise of the test tool.

4. The test tool according to claim 1, wherein the pinching recess or the pinching projection includes a curved surface for contact with a fingertip.

5. The test tool according to claim 1, wherein the electrodes include a first electrode electrically connected to the analyzing circuit, and also include a second electrode cooperating with the first electrode to apply a voltage across a target portion at the test tool, the second electrode working as the counter-disturbance noise electrode.

6. The test tool according to claim 1, wherein one of the terminals of the analyzing device is grounded as a ground connection terminal, wherein the counter-disturbance noise electrode is brought into contact with the ground connection terminal when the test tool is attached to the analyzing device.

7. The test tool according to claim 1, wherein the counter-disturbance noise electrode is arranged to surround at least said another electrode.

8. The test tool according to claim 1, further comprising: a path for moving the sample; and a cover laid over the base plate and formed with an outlet for discharging air out of the path, wherein the counter-disturbance noise electrode is formed along an edge of the base plate.

9. The test tool according to claim 1, wherein the counter-disturbance noise electrode contacts a corresponding one of the terminals earlier than said another electrode, when the test tool is attached to the analyzing device.

10. The test tool according to claim 1, designed as a biosensor for measuring a blood-sugar level.

11. A test tool attached to an analyzing device for sample analysis, the analyzing device including a plurality of terminals and an analyzing circuit, the test tool being mutually attached to or removed from the analyzing device, the test tool comprising:

a pinching portion used for attachment to the analyzing device or for removal from the analyzing device; and a plurality of electrodes brought into contact with the terminals when the test tool is attached to the analyzing device;

wherein at least one of the electrodes serves as a counter-disturbance noise electrode that is more likely to receive disturbance noise than another electrode;

wherein the counter-disturbance noise electrode is partly exposed at the pinching portion; and wherein the electrodes include a first electrode electrically connected to the analyzing circuit, and a second electrode cooperating with the first electrode to apply a voltage across a target portion at the test tool, the second electrode working as the counter-disturbance noise electrode.

12. A test tool attached to an analyzing device for sample analysis, the analyzing device including a plurality of terminals and an analyzing circuit, the test tool being mutually attached to or removed from the analyzing device, the test tool comprising:

a pinching portion used for attachment to the analyzing device or for removal from the analyzing device; and a plurality of electrodes brought into contact with the terminals when the test tool is attached to the analyzing device;

wherein at least one of the electrodes serves as a counter-disturbance noise electrode that is more likely to receive disturbance noise than another electrode;

wherein the counter-disturbance noise electrode is partly exposed at the pinching portion;

wherein one of the terminals of the analyzing device is grounded as a ground connection terminal;

wherein the counter-disturbance noise electrode is brought into contact with the ground connection terminal when the test tool is attached to the analyzing device.

* * * * *

UNITED STATES PATENT AND TRADEMARK OFFICE
CERTIFICATE OF CORRECTION

PATENT NO.        : 7,651,595 B2                                      Page 1 of 1
APPLICATION NO. : 10/545394
DATED             : January 26, 2010
INVENTOR(S)       : Doi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 884 days.

Signed and Sealed this

Twenty-third Day of November, 2010

David J. Kappos
*Director of the United States Patent and Trademark Office*